United States Patent
Rhodes et al.

(10) Patent No.: US 6,478,942 B2
(45) Date of Patent: Nov. 12, 2002

(54) METHOD AND APPARATUS FOR ELECTROPHORETIC FOCUSING

(76) Inventors: Percy H. Rhodes, 412 Westburg Ave., Huntsville, AL (US) 35801; Robert S. Snyder, 1515 Monte Sano Blvd., Huntsville, AL (US) 35801

( * ) Notice: Subject to any disclaimer, the term of this patent is extended or adjusted under 35 U.S.C. 154(b) by 0 days.

(21) Appl. No.: 09/730,834

(22) Filed: Dec. 7, 2000

(65) Prior Publication Data

US 2001/0000103 A1 Apr. 5, 2001

Related U.S. Application Data

(62) Division of application No. 09/277,944, filed on Mar. 29, 1999, now Pat. No. 6,171,466.

(51) Int. Cl.$^7$ ............................. G01N 27/26; C02F 1/48
(52) U.S. Cl. ....................................... 204/450; 204/554
(58) Field of Search ................................ 204/450, 465, 204/518, 600, 615, 644, 666, 670, 671; 210/748

(56) References Cited

U.S. PATENT DOCUMENTS

| | | |
|---|---|---|
| 3,149,060 A | 9/1964 | Dobry et al. |
| 3,412,008 A | 11/1968 | Strickler |
| 4,309,268 A | 1/1982 | Richman |
| 4,362,612 A | 12/1982 | Bier |
| 4,588,492 A | 5/1986 | Bier |
| 4,752,372 A | 6/1988 | Rhodes et al. |
| 5,336,387 A | 8/1994 | Egen et al. |

OTHER PUBLICATIONS

Rhodes et al., "Electrohydrodynamic Distortion of Sample Streams in Continuous Flow Electrophoresis", Journal of Colloid and Interface Science, vol. 129, No. 1, Apr. 1989, pp. 78–90.

Ivory et al., "Continuous Counteracting Chromatographic Electrophoresis", Biotechnol. Prog. 1980, 6, 21–32.

*Primary Examiner*—Jill Warden
*Assistant Examiner*—Alexander Stephan Noguerola
(74) *Attorney, Agent, or Firm*—Larson & Taylor PLC

(57) ABSTRACT

An apparatus and method is provided for obtaining a preparative-scale, free-fluid electrophoretic separator with high resolution as well as an analytical capability commensurate with capillary zone electrophoresis. The electrophoretic focusing apparatus and method of the present invention combines features of electrophoresis and isoelectric focusing to accomplish large scale purifications and fractionations that have not previously been possible, and features a separation chamber bounded by precision-pore, insulated screens, a plurality of purge chambers, a plurality of electrode chambers, and a plurality of pump means. The separation device of the invention is capable of high speed of separation and short residency of sample through the use of high voltage gradients which are produced by relatively low voltages applied across the narrow chamber dimensions. The present invention is also highly flexible, with operation in either a constant electric field, continuous flow mode or in a linearly varying electric field, batch mode, and both modes permit scanning of the sample fraction content and display in a conventional histogram format. The present apparatus and method thus achieves high resolution of separation in an analytical or a preparative mode through a practically unlimited scale-up potential, and controls the adverse effects of Joule heating and electrohydrodynamics on the electrophoretic separation procedure.

20 Claims, 9 Drawing Sheets

METHOD AND APPARATUS FOR ELECTROPHORETIC FOCUSING

This application is a divisional application of U.S. application Ser. No. 09/277,944 filed Mar. 29, 1999 now U.S. Pat. No. 6,171,466.

FIELD OF THE INVENTION

The invention relates in general to an apparatus and method for achieving electrophoretic focusing, and in particular to an apparatus for achieving electrophoretic separation and purification which is characterized by a separation chamber formed between two precision-pore, insulated screens and which also includes inlet and outlet ports, a plurality of purge chambers for extracting extraneous fractions and for providing thermal cooling, a plurality of electrode chambers to provide a transverse electric field in the separation chamber, and pumping means sample, carrier buffer and electrode rinse buffer through the apparatus, and a method of employing this apparatus to achieve separation and collection of a desired component from a biological or chemical sample.

BACKGROUND OF THE INVENTION

There are two electrokinetic methods that have had success separating biological materials, namely, zone electrophoresis and isoelectric focusing. Electrophoresis is the movement of suspended or dissolved charged particles in response to an applied electric field. The rate of motion depends upon the charge, size and shape of the particles and specific properties of the solvent buffer and its container. In zone electrophoresis, the components in a short sample zone are separated by the action of the electric field. The injection of a narrow, uniform zone and the absence of dispersive fluid flows are necessary conditions for successful operation. Significant sources of dispersion are: 1) uneven (parabolic) flows; 2) electrohydrodynamic flows; 3) molecular diffusion; 4) thermal convection; 5) sedimentation; 6) thermally induced sample mobility variations; and 7) electroosmosis.

In continuous zone electrophoresis (CFE), the electrolyte solution flows in a direction perpendicular to the electric field and the mixture to be separated is inserted continuously into the flowing solution. Components of the mixture are deflected according to their electrophoretic mobilities and can be collected continuously after their migration. Svensson and Brattsten were the first to report a method for carrying out electrophoresis continuously. They used a lateral electric field in a narrow plexiglas box packed with glass powder as an anti-convective medium. Durrum modified the above configuration by replacing the glass-filled box with a filter paper curtain, hanging in a free vapor space. While both of these methods demonstrated continuous electrophoresis, they both used a stabilizing medium. Anti-convective media cause many problems such as reduction of the flow capacity by their presence, electroosmosis in the interstices, adsorption of the sample and "packing or eddy diffusion". Efforts were then made to do continuous electrophoresis in a free fluid. Bier in 1957 reported the first continuous flow electrophoresis device which could separate two protein solutions by adjusting the buffer pH relative to the isoelectric point of one of the solutions. The device which he described as "continuous free-boundary flow electrophoresis" did not take place in a single rectangular chamber and did not produce a separation of high purity. Dobry and Finn (U.S. Pat. No. 3,149,060) were the first to report continuous flow free fluid electrophoresis in a rectangular chamber with a cross-section of low aspect ratio, hence providing little resistance to thermal convective flow disturbances. This configuration was limited to very low electric fields and required the use of buffer thickening agents to suppress convective eddies. Philpot described a continuous flow electrophoresis system with the electric field applied across (perpendicular to) a thin film of liquid. He later wrapped his thin film geometry into a thin annulus surrounded by two concentric cylinders (electrodes). The outer cylinder rotated to provide a stabilizing velocity gradient.

Although a large throughput, 10 g/hr, was accomplished by the Biostream, its resolution was poor. This was followed by forced flow electrophoresis devised by Bier for the large scale purification of a single component in a mixture. Giddings extended this development with field flow fractionation wherein an electric field has been just one example of the force field deflecting the sample across the narrow plane. The need for flat, uniform surfaces that also serve to isolate the electrode arrays have slowed this development. Mel in 1959 reported the first use of a high aspect ratio rectangular separation chamber using a lateral electric field. The "thin" chamber of 0.7 cm thickness provided the necessary wall interaction to suppress thermal convective flows to the extent that a less viscous free flow buffer could be used. This design served as the impetus for the development of the conventional CFE machines of the 60's and 70's with their chamber cross-section of high aspect ratio and laterally directed electric fields. During this time frame, Hannig and his co-workers developed CFE by making the chamber cross-sections even thinner, approaching 0.25 cm for some designs. Unfortunately, the gains made in suppressing thermal convection were wiped out by electrohydrodynamic interaction with intrinsic chamber fluid flows to cause crescent-shaped distortions. Nevertheless, a variety of CFE instruments were manufactured according to the designs of Hannig (in Germany) and Strickler (in the US) (U.S. Pat. No. 3,412,008) and several hundred instruments were used in laboratories around the world. Rhodes and Snyder subsequently devised a technique to minimize these flow distortions (U.S. Pat. No. 4,752,372).

The concept of counterflow to oppose the electrophoretic migration was first described to the inventors by Griffin and McCreight as a means to attenuate the crescent shaped distortion in CFE chambers. Richman subsequently patented a similar counter-flow method where axial bands of electroosmotic coatings of varying zeta potential would "straighten" distorted sample bands (U.S. Pat. No. 4,309,268). The method was impractical because most coatings change with time and there exists no spectrum of coatings with respect to zeta potential. A more practical approach that did not use counter-flow was suggested by Strickler wherein the CFE was divided into two vertical compartments, each with a different wall coating, so that the combined electroosmotic flow would yield a more coherent sample band. Subsequently, Ivory used counter-flow to increase sample residence time in a recycling CFE. Egen, et al. have also devised a counter-flow gradient focusing method (U.S. Pat. No. 5,336,387).

While the crescent phenomenon was long known to cause untenable sample stream distortion in CFE instruments, it was not until 1989 that Rhodes and Snyder showed that electrohydrodynamics transforms initially circular sample streams into ribbons that initiate the crescent shaped distortions. The operation of CFE devices was labor intensive and unreliable due to contamination of the closely spaced chamber walls and the resultant electroosmotic flow variations through the chamber.

Isoelectric focusing (IEF) is an electrophoretic technique that adds a pH gradient to the buffer solution and together with the electric field focuses most biological materials that are amphoteric. Amphoteric biomaterials such as proteins, peptides, nucleic acids, viruses, and some living cells are positively charged in acidic media and negatively charged in basic media. During IEF, these materials migrate in the pre-established pH gradient to their isoelectric point where they have no net charge and form stable, narrow zones. Isoelectric focusing yields such high resolution bands because any amphoteric biomaterial which moves away from its isoelectric point due to diffusion or fluid movement will be returned by the combined action of the pH gradient and electric field. The focusing process thus purifies and concentrates sample into bands that are relatively stable. This is a powerful concept that has yielded some of the highest resolution separations, especially when coupled with electrophoresis in two-dimensional gels. Unfortunately there are drawbacks to IEF that have limited its applications. The rate of electrophoretic migration of each charged species decreases progressively as it approaches its isoelectric point and long residence times are required for high resolution. Proteins have reduced solubility at their isoelectric point although precipitation of the concentrated bands can be minimized by addition of detergent. Additional problems relate to the commercial amphoteric solutions, including: 1) difficulty of extracting the separated proteins, peptides, etc., from the amphoteric solutions because of their similar physical properties and interactions; 2) chemical toxicity; 3) handling problems; and 4) cost.

IEF had its practical beginning in the mid-1950's when Kolin first demonstrated the concept of focusing ions in a pH gradient by placing a molecular sample between an acidic and a basic buffer and applying an electric field. Although the constituents focused rapidly, the gradient soon deteriorated due to the concurrent electrophoretic migration of all of the buffering ions. The synthesis of stable carrier ampholytes by Vesterberg and their successful commercial development led to broad use in gels or other restrictive media to suppress electroosmosis and thermal convection during analytical separations.

The high resolution achieved by IEF encouraged many attempts to develop a preparative version of the process. This proved to be much more difficult for IEF than zone electrophoresis because of the variable fluid properties and sample characteristics within the chamber leading to changing values of electroosmosis and thermal convection during the separation. Various CFE devices were modified to run with an amphoteric mixture instead of buffer but the problems (long focusing time requiring a slow flow through the chamber, pH drift toward the cathode, reduced voltage/current levels for acceptable heating and convection) became insurmountable. A. J. P. Martin described a means of performing large-scale isoelectric focusing by connecting a number of separation chamber in series via membranes. By circulating the fluids in each compartment through external coolers, Martin claimed that the removal of heat had been solved. Since the only pH shift occurred across the membranes, the pH gradient was quite steep between chambers. Bier further developed the external cooling system, added sensors and demonstrated the improved focusing with recycling (U.S. Pat. No. 4,362,612). Bier added a stabilizing assembly rotation to the membrane segmentation and a novel collection system (U.S. Pat No. 4,588,492) which led to the Roto-Phor from Bio-Rad (Hercules, Calif.). Righetti has also extended the multi-compartment concept by using membranes, cast and polymerized with the desired amphoteric molecules inside, to establish the pH gradient rather than preparing a constant pH in each compartment. The Iso-Prime system (Hoefer Instruments, San Francisco, Calif.) is based upon a stack of membranes with buffer between them. The pH gradient develops rapidly and the proteins move through the membranes until they reach the cell with the pH equal to their isoelectric point. Although the membranes stabilize the focusing process, they become clogged if the protein precipitates in them.

Thus, prior methods of isoelectric focusing have suffered from the many drawbacks outlined above, and have also been hindered by problems during the transition from an analytical system to a preparative system that have limited its intended use. It is thus highly desirable to develop a focusing system for separating biological molecules and other components in a mixture which is able to avoid all of the problems of the prior art and which can achieve high resolution of separation in an analytical or a preparative mode through a practically unlimited scale-up potential. It is also highly desirable to develop an electrophoretic focusing system which can control the adverse effects of Joule heating and electrohydrodynamics on the electrophoretic separation procedure.

SUMMARY OF THE INVENTION

It is an object of the present invention to provide a preparative-scale free-fluid electrophoretic separator with high resolution as well as an analytical capability commensurate with capillary zone electrophoresis. The particular mode of high-resolution separation as provided by the present invention, which is referred to as electrophoretic focusing, combines features of electrophoresis and isoelectric focusing to accomplish large scale purifications and fractionations that have not been possible before now.

It is another object of the present invention to develop a separation device capable of high speed and short residency through the use of high voltage gradients. These high voltage gradients are produced by relatively low voltages applied across the narrow chamber dimensions. Another object is flexibility with operation in either a constant electric field, continuous flow mode or in a linearly varying electric field batch mode. Both modes permit scanning of the sample fraction content and display in a conventional histogram format. The goal of high resolution of separation can be achieved through the use of the present invention in an analytical or a preparative mode through a practically unlimited scale-up potential. A further goal is to control the adverse effects of Joule heating and electrohydrodynamics.

These and other objects and benefits are achieved by the use of the present invention which provides a number of innovations and insights with regard to fundamental fluid and thermal geometries and operations. The focusing is accomplished with a minimum of sample migration which leads to a higher resolution in a shorter time. Adiabatic thermal conditions in the lateral (scale-up) dimension permit a large increase in throughput at no apparent loss of resolution. Active cooling limits the maximum chamber temperature and its relationship to the chamber orientation and buffer fluid transport is such as to limit thermal convection. Porous, rigid screens permit a controlled focusing cross-flow which balances the electrophoretically-driven sample velocity.

DETAILED DESCRIPTION OF THE PREFERRED EMBODIMENTS

Figure 1:
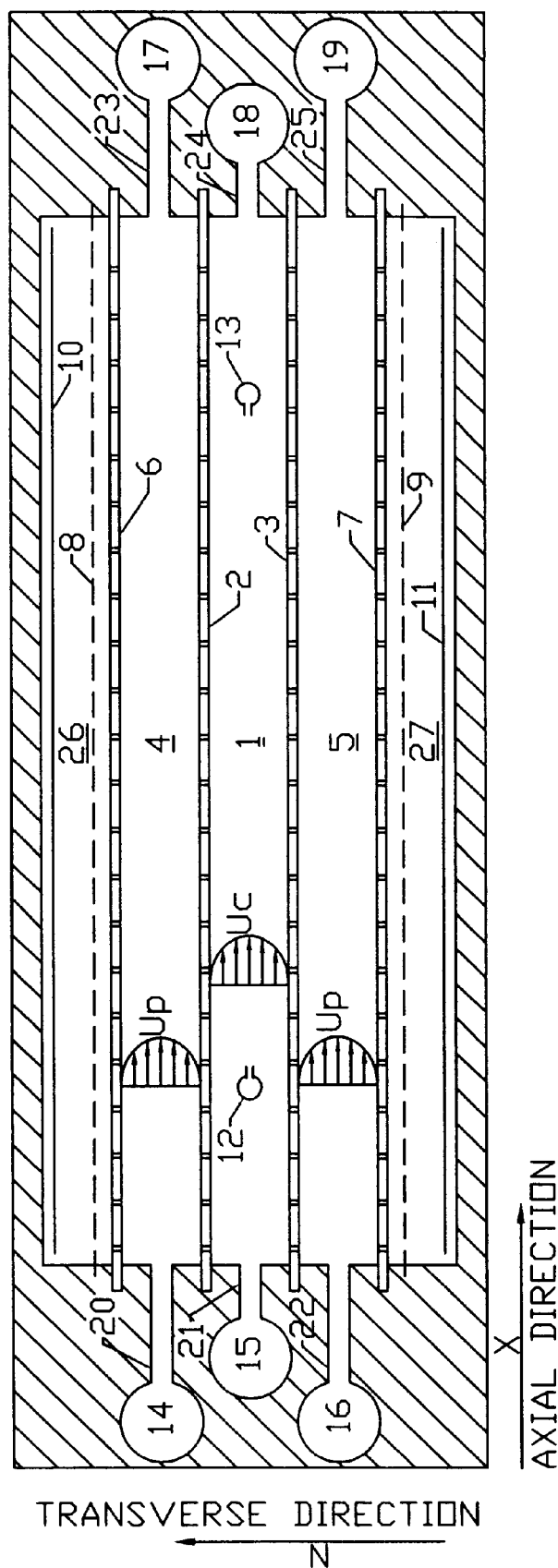
FIG. 1 is a side schematic view of the separation chamber of the present invention, taken in the axial and transverse directions.

In accordance with the present invention, there is provided an electrophoretic focusing apparatus and method which is useful in achieving the separation and purification of particular components of a mixture of biological or chemical materials. The general purpose of the invention is a continuous processing system that separates and purifies any soluble or microparticulate sample that acquires a surface electric charge when immersed in a polar (e.g. aqueous) fluid environment. It combines the best features of electrophoresis and isoelectric focusing in a novel device that incorporates a combination of transverse electric field gradient and buffer flow field to focus and collect any selected biological component. Although the high resolution achievable by focusing is familiar to isoelectric focusing, electrophoretic focusing avoids many of its problems, such as the need for complex buffers and the long times required for the molecules to reach their isoelectric point. This new concept incorporates a large-gap chamber and control of all sources of sample dispersion. The design of the electrophoretic focusing chamber combined with the orientation and magnitude of the electric fields and buffer flows are planned to eliminate sample dispersion. The large gap will keep sample away from the walls as well as increase its throughput.

Many research and applications tasks with biological materials require a large source of highly purified biologically active molecules. The diverse supply of materials for biotechnology ranging from plants to genetically derived sources are placing increased demands on separation and purification. Existing preparative separation techniques yield products with a variety of impurities that can be measured analytically but not removed. Analytical techniques have been perfected in recent years but attempts to scale these techniques into larger production have relied on generally increasing the physical dimensions instead of investigating a new technique. It is an advantage of the focusing device of the present invention that it will be able to purify biological materials in amounts and to purity levels above those now obtainable.

The principle of electrophoretic focusing utilized in conjunction with the present invention consists of opposing the electrophoretic sample velocity with a uniform fluid flow transverse to the direction of carrier flow through the chamber. Basically, this is the concept of counterflow which is discussed above. The uniqueness of this invention is how this principle is used in conjunction with both constant and varying voltage fields to achieve a novel and powerful method of continuous sample separation. This result is achieved by using a combination of electrode arrays and insulated screens to provide the electric field gradient and uniform transverse flow necessary for focusing.

If the electric field is configured in the transverse direction (instead of the lateral direction as with CFE), electroosmotic flow becomes negligible and the viscous parabolic flow is orthogonal to the migration direction and hence also ceases to be a factor. Since the transverse migration is now in the narrow chamber dimension, the sample residence time is quite short and resolution will suffer. However, if a cross-flow is used, the sample will be held in the chamber by the cross-flow, thus improving the resolution by some calculatable amount. This solution to the problems of CFE has been considered by past inventors but the problem of the area electrode/chamber broad wall has kept this idea from realization. As the details of the invention show, this problem is solved by a unique utilization of micro-pore, thin, rigid, insulating screens.

The electrophoretic separator of the present invention is primarily characterized by a separation chamber formed between two precision-pore, insulated screens. The perforations permit transverse fluid flow through the chamber to effect a separation of one or multiple species and also to provide cooling in the chamber interior. This unique use of cross-flow focuses one sample fraction continuously in the chamber when using a constant electric field to oppose the cross-flow or alternatively focuses a mobility spectrum of the sample in the chamber when using a linearly varying electric field. Since the separation is carried out in the direction transverse to the carrier buffer flow, the focusing is accomplished with a minimum of sample migration which leads to a higher resolution in a shorter time. The relatively short transverse dimension allows the use of a high voltage gradient derived from a low source voltage. When using low voltage gradients (to 100 V/cm), the sample is injected and collected in singular or multiple ports so that the chamber is only partially filled with sample. At voltage gradients from 100 V/cm to 1000 V/cm, the chamber thickness is greatly reduced so that the sample fills the entire chamber. This configuration provides a homogeneous medium between the chamber walls and eliminates conductivity gradients which produce destructive circulatory flows through Joule heating and electro-hydrodynamics.

Another problem with CFE is the method of sample collection. The separated fractions must be collected by a finite number of collection ports which ultimately limit resolution. Collection for a batch process, such as chromatography or capillary electrophoresis (CE), poses no such problem as each separate fraction can be individually collected over a variable time interval rather than a limited fixed distance interval between each adjacent collection port as with CFE. This invention can collect fractions as a function of time by varying the crossflow velocity to produce a histogram similar to that obtained from chromatography or capillary electrophoresis.

The present invention is capable of operation as a true focusing device in the same manner as IEF except that no pH gradient is utilized. A linear varying electric field gradient is produced by an electrode array with a parabolic voltage distribution impressed on the array. This system uses a homogeneous conventional buffer system in contrast to the complex, multi-component systems needed for conventional IEF. Since electrophoretic focusing can be done with either a constant voltage gradient or with a linearly varying voltage gradient, the two respective configurations of the present invention will be described separately.

I. Constant Voltage Gradient Configuration

Figure 2:
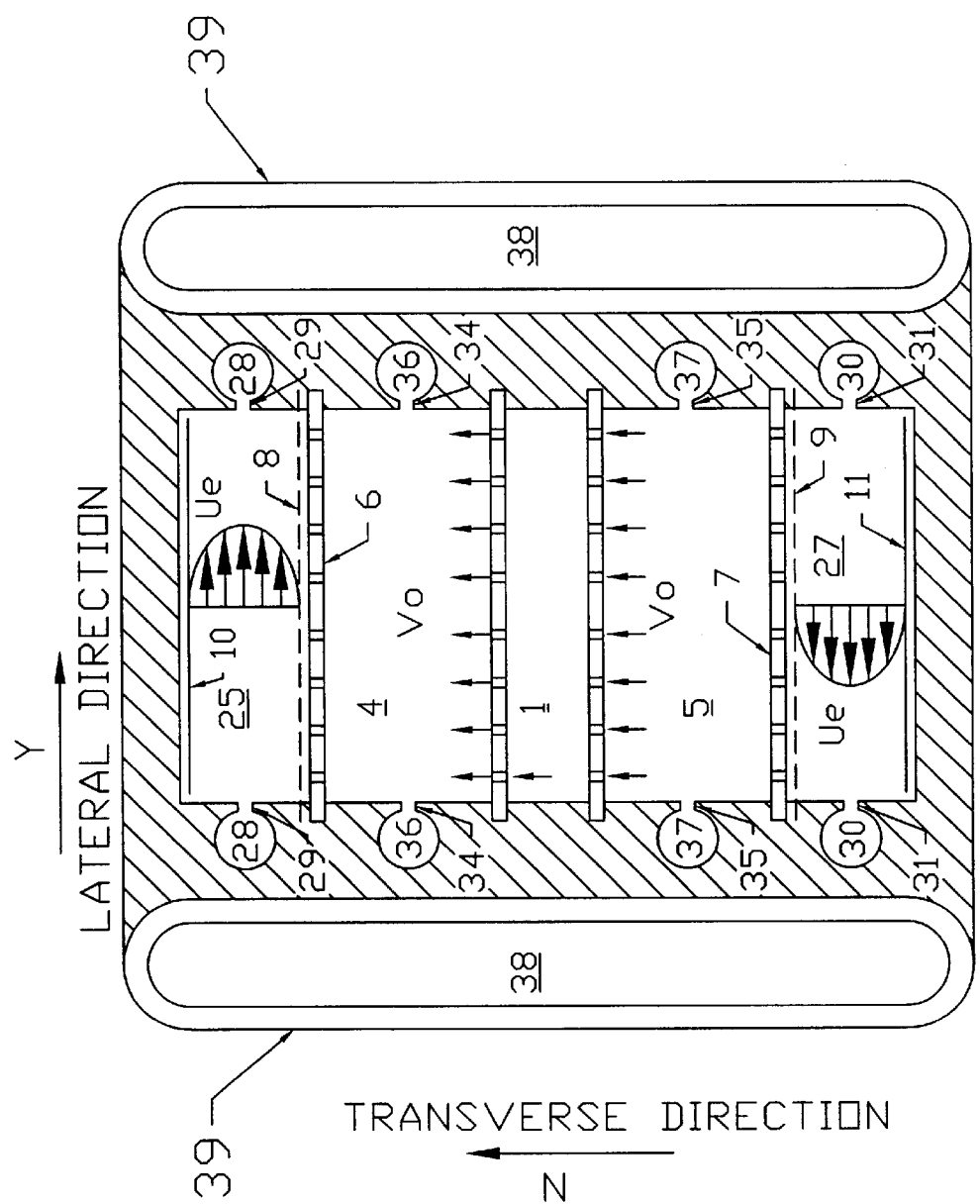
FIG. 2 is a side schematic view of the separation chamber of the present invention, taken in the lateral and transverse directions.
Figure 3:
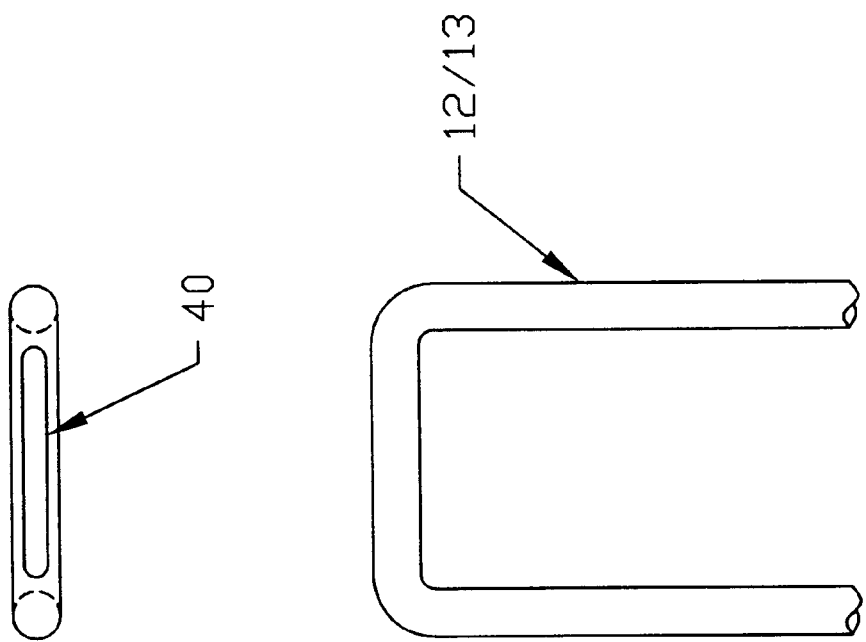
FIG. 3 is a schematic view of one of the injector/collectors of the present invention.
Figure 9:
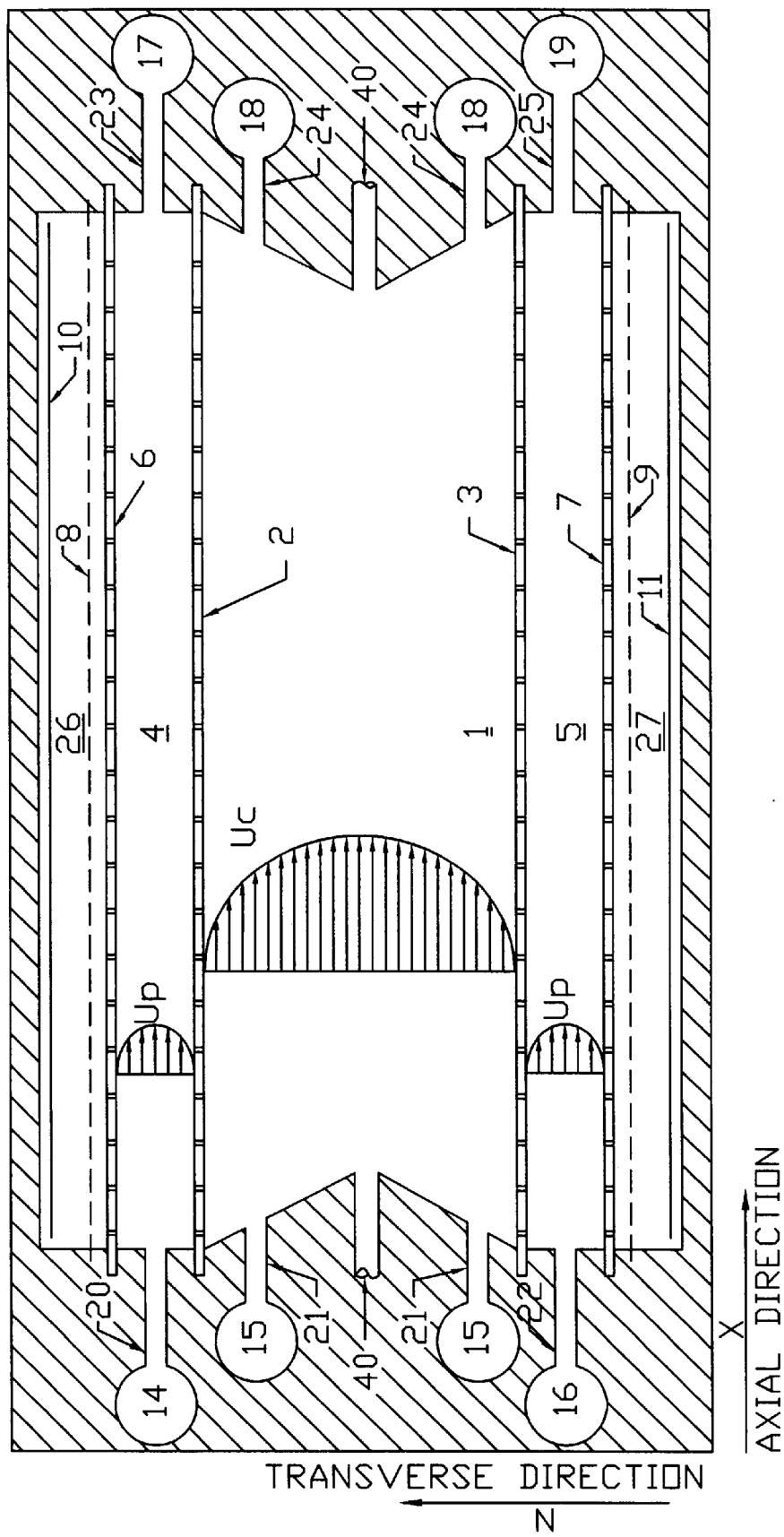
FIG. 9 is a side schematic view of an alternative embodiment of the separation chamber of the present invention, taken in the axial and transverse directions.

FIGS. 1 and 2 show the total chamber (or simply, the chamber) and the different flow regions. The chamber is comprised of a plurality of flow regions or sub-chambers, such as the five elements 1, 4, 5, 26, and 27 shown in FIG. 1. In the preferred embodiment, the separation chamber 1 is bounded by two fine mesh precision-pore, insulated screens, 2 and 3. Carrier buffer enters the separation chamber through the inlet manifold 15 and port 21. The buffer flows through the chamber as shown with a center plane velocity of $U_c$ and exits the separation chamber via the exit port 24 and manifold 18. Sample is injected in the form of a lamina through the injection port 40 in the injector 12 shown in detail in FIG. 3. The injector is made of glass-coated metal tubing and located in the chamber as FIG. 2 shows. Note that the sample lamina does not fill the entire separation chamber width (y-direction). Separated sample is collected through slit 40 in the collector 13. Sample can still be injected as a lamina through an injection port 40 without requiring the injector 12 by placing the injector port 40 in the center of the separation chamber entrance wall. Carrier buffer will now enter the separation chamber through flanking buffer entry ports 21 and associated manifolds 15 located in each edge of the entrance wall. The converging buffer flows will reduce the thickness of the sample lamina. In a similar manner, separated sample can be collected through a collection port 40 located in the center of the separation chamber exit wall with the buffer exiting the chamber through two flanking ports 24 and manifolds 18 located in each exit wall, as illustrated in FIG. 9.

As best shown in FIG. 1, adjacent co-directed Uptake place in the purge chambers 4 and 5. These flows enter through inlet manifolds 14, 16 and inlet ports 20, 22. The flows exit through the manifolds 17, 19 and ports 23, 25. An electric field $E_o$ is impressed in the chamber by electrodes 10 and 11. These electrodes are located respectively in electrode chambers 26 and 27. Rinse flows of center plane velocity $U_e$ take place in these chambers through manifolds 28, 30 and ports 29, 31. Membranes 8, 9 isolate the electrode chambers to contain electrolysis gas and products which are swept away by the electrode rinse flow $U_c$. The membranes 8, 9 are rigidized by the precision-pore, insulated screens 6, 7. This is accomplished by keeping the pressure in the electrode chambers greater than that in the rest of the chamber. This allows electric current to flow through the membranes while keeping electrolysis products and flow disturbances confined to the electrode chambers. A focusing flow velocity $V_o$ is established in the separation chamber 1 by a fluid flow which enters through inlet ports 35 and manifolds 37 located in the purge chamber 5. This flow exits the purge chamber 4 through exit ports 34 and manifolds 36. This flow $V_o$ is rendered uniform in the separation chamber by virtue of the small pores in screens 2 and 3 (e.g., roughly 0.006 inch diameter) and the large purge chamber volume which serves as a flow manifold. Two evacuated (38) glass walls 39 bound the chamber in the lateral dimension as FIG. 2 shows.

It is important to eliminate lateral temperature gradients in the separation chamber 1. The laterally directed electrode rinse flows $U_e$ could possibly cause lateral temperature gradients to exist in the separation chamber 1. For this reason, the rinse flows in the electrode chambers are oppositely directed as FIG. 2 shows. To further attenuate these lateral temperature gradients, baffles can be placed laterally in the electrode chambers and spaced in the axial direction. Flows in alternating directions can then be impressed by an appropriate manifold system. These lateral temperature gradients originating in the electrode chambers are further averaged out by the purge flow Up taking place in the purge chambers 4 and 5.

If the upper electrode 10 is negative and the bottom electrode 11 is positive, an electric field $E_o$ exists in the separation chamber 1 which will cause a negatively charged sample to migrate down (transverse direction) under the influence of the electric field $E_o$ against the uniform transverse focusing flow velocity $V_o$. Consider a sample fraction of electrophoretic mobility, $\mu_i = V_o/E_o$ that has been injected through the port 12 located on the separation chamber center plane. The sample fraction $\mu_i$ will remain at the center plane of the separation chamber 1 and move through it with a carrier buffer velocity $V_c$ and be collected at the exit port 13. All other sample (mobility different than $\mu_i$) will exit either through port 24 in the separation chamber or through ports 23 and 25 in the purge chambers. A sample fraction scan can be made by varying $V_o$. The effluent from collection port 13 enters an ultraviolet detector and is displayed as a conventional histogram.

Thus, by varying the transverse focusing flow $U_o$ against a constant electric field $E_o$, a scan of the fraction content of a sample can be made. This type of scan of a sample is unique in a separation device since the peak histogram is a function of the time rate of change of the focusing velocity $V_o$ and is given by $\mu_i = V_o/E_o$. The time rate of change $V_o$ is controlled by a precision computer controlled pump. This allows real time control of the separation process. Continuous sample collection can be made by stopping the scan at a peak of interest, or made after the complete scan has been made by recovering the transverse velocity $V_o$ corresponding to a peak of interest.

The peak values are detected by a liquid chromatography flow cell and detector system and fed back into the computer to achieve a feed-back control system. Cooling of the electrode chambers 26, 27 is provided by the electrode rinse flow while the purge flow Up provides cooling for the rest of the chamber. The flow velocity $U_p$ in the purge chambers 4, 5 may be up to ten times that in the separation chamber 1 in order to accomplish this purpose. The pore size of the screens 2, 3 is small (presently 0.006 inch hole, 34% open area) and thickness 20 gauge. While the small holes will dampen disturbance flows between the separation chamber 1 and the purge chambers 4, 5, it is advisable to consider pressure drops in the separation and purge chambers so that $b_p^2/b_c^2 = U_p/U_c$ where $b_p$ and $b_c$ are the thicknesses of the purge and separation chambers respectively. The port 40 shown in FIG. 3 confines the sample stream to the center region of the chamber. This configuration avoids the adverse effects of electroosmotic flows at the end walls. The evacuated glass side walls 39 preclude heat transfer in the lateral direction as FIG. 2 shows. This condition eliminates any variance in this direction so that scale-up of the sample stream width is unlimited.

Referring to FIG. 2, the focusing flow $V_o$ causes a temperature gradient in the transverse direction as it brings cooler flow from the purge chamber 5 into the separation chamber 1. Also, referring to FIG. 1, the purge flow which cools the separation chamber is heated as it moves through the chamber giving rise to an axial temperature gradient in the separation chamber. The first gradient gives rise to a clockwise circulation when the chamber is in the vertical orientation, while the second gradient gives rise to a similar clockwise circulation when the chamber is in the horizontal orientation. Mathematical models show that the circulations are attenuated to a much greater extent by the chamber walls when the chamber is in the horizontal orientation. However, by utilizing internal injection and collection ports 12, 13 the effect of the circulations is eliminated since the disturbance flows occur in the front of port 12 and behind port 13 and hence does not affect the separation. Thus there is no effect of chamber orientation on thermal convection disturbances with internal injection and collection ports. The above configuration is adaptable to voltage gradients up to about 100 V/cm. However, if higher voltage gradients are preferred, some modification should be considered.

The high voltage (second) configuration is characterized by a very thin (transverse thickness) separation chamber and the elimination of the internal injection and collection ports 12 and 13. Sample is injected through port 21 and collected through port 24. Hence, sample fills the entire separation chamber with no buffer zones which characterize the low voltage configurations. The smaller heated volumes of the separation and purge chambers limit the chamber temperature at high electric fields. A significant advantage of having only sample in the separation chamber is the homogeneity of the electrical conductivity in the field direction. Since Joule heating and electrohydrodynamics both vary as the electric field squared, and since the adverse effects of both are dependent on electric field gradients, it is important to eliminate these gradients if high voltage gradients are to be successfully used. The high voltage configuration must be operated in the horizontal orientation. While lateral gradients are controlled by the insulated ends 39, transverse temperature gradients can be significant at high voltage gradients and are exacerbated by the cool focusing cross-flow from purge chamber 5 into the separation chamber. The focusing flow $V_o$ produces a gradient of increasing temperature from purge chamber 5 through the separation chamber to purge chamber 4. This gradient can give rise to significant circulation if the chamber is operated in the vertical orientation aligned with gravity. If the chamber is operated in the horizontal orientation, this circulation is suppressed as our mathematical models of the chamber configuration have shown. Since the chamber is cooled by the purge flows of velocity $U_p$ emitting from the purge manifolds, an axial temperature gradient is also developed in the chamber, however, it is generally much smaller than that produced by the transverse gradient and is similarly suppressed by horizontal operation.

II. Varying Voltage Gradient Configuration

Figure 4:
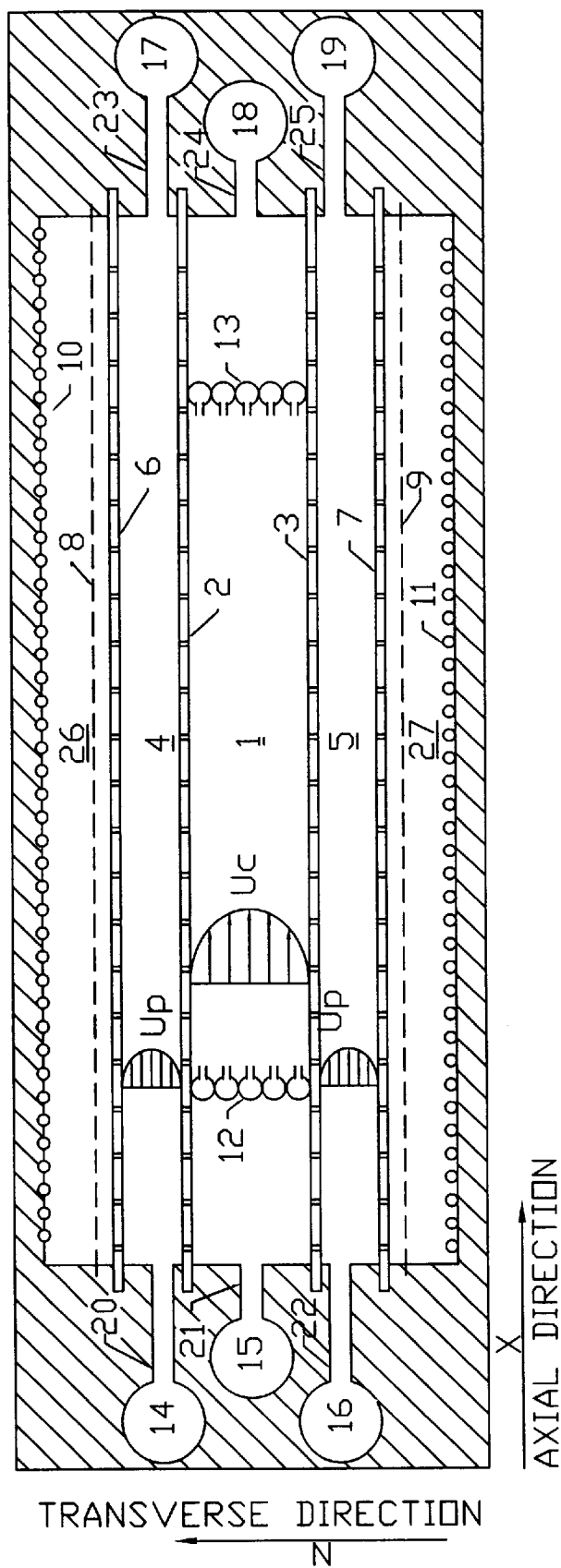
FIG. 4 is a side schematic view of an alternative embodiment of the separation chamber of the present invention, taken in the axial and transverse directions.
Figure 5:
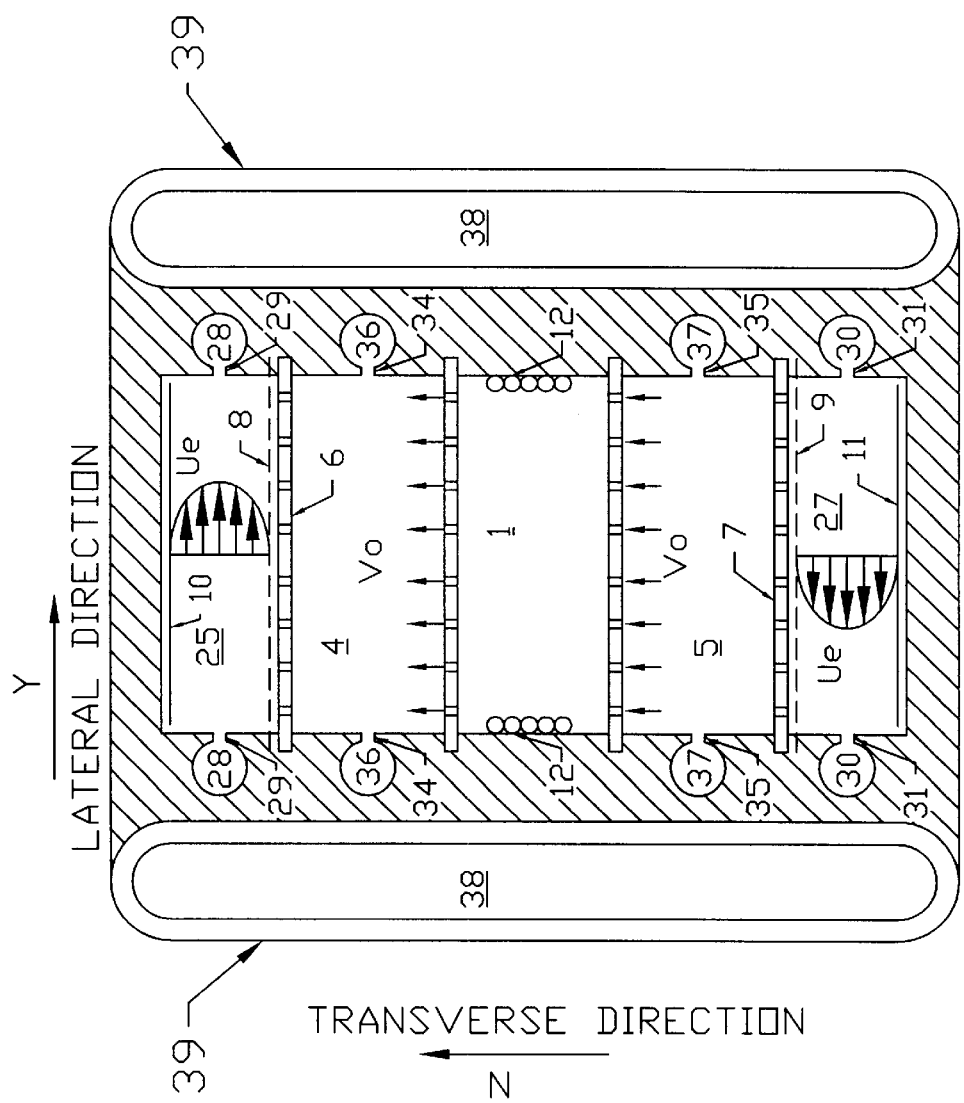
FIG. 5 is a side schematic view of an alternative embodiment of the separation chamber of the present invention, taken in the lateral and transverse directions.
Figure 6:
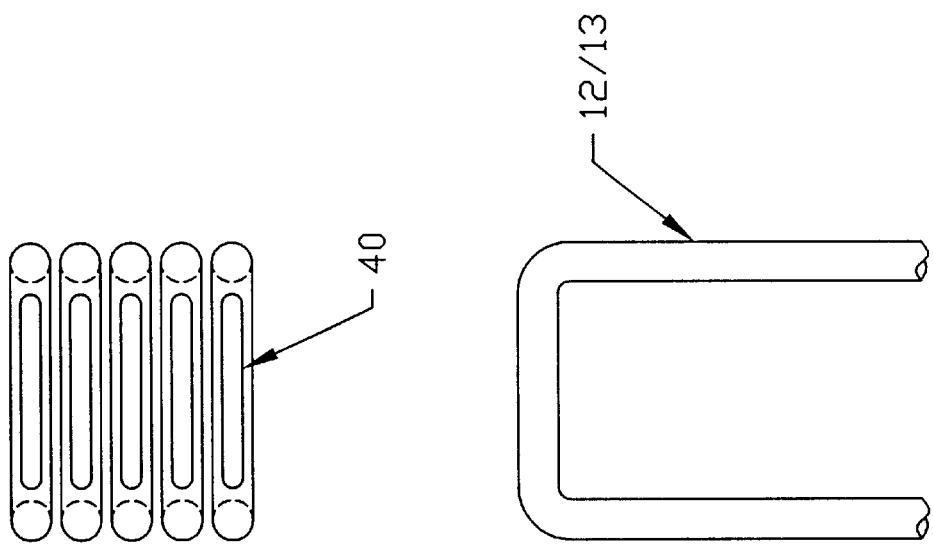
FIG. 6 is a schematic view of an alternative embodiment of one of the injector/collectors of the present invention.

The third configuration shown in FIGS. 4, 5 and 6 can be described as a true focusing system. The significant features of this innovation are the use of a constant transverse flow and a varying transverse electric field that is linear in the transverse coordinate. The electric field can be described by:

$$E_z = B - Cz,$$

where z is perpendicular to the direction of the carrier buffer flow, B is the field at z=0 and C is a linear constant. The corresponding electrophoretic velocity of sample fraction i is:

$$v_e = \mu_i E_z = \mu_i (B - Cz)$$

Focusing is achieved by the imposition of a constant fluid flow of speed $V_o$ with a direction opposing $v_e$. The velocity of a single ionized molecule of the $i^{th}$ sample fraction is:

$$dz_e/dt = -V_o + \mu_i(B - Cz) \tag{1}$$

where $z_e$ is the electrophoretic displacement of the fraction in the z-direction. Each fraction approaches a null position $Z_i$ given by:

$$V_o = \mu_i(B - Cz_i) \tag{2}$$

Solving equation 1, $$z_e = (z_o - z_i) \exp(-\mu_i C t) + z_i \tag{3}$$

where $z_o$ is the initial ion position. For large t, the first term approaches zero so that the final (focused) position $z_i$ is independent of the initial position, $z_o$, and is the position obtained from equation 2. The advantage of focusing is that each fraction moves toward a fixed position in the separation chamber. This is in contrast to zonal techniques where fractions move to relative positions with respect to other fractions.

Figure 7:
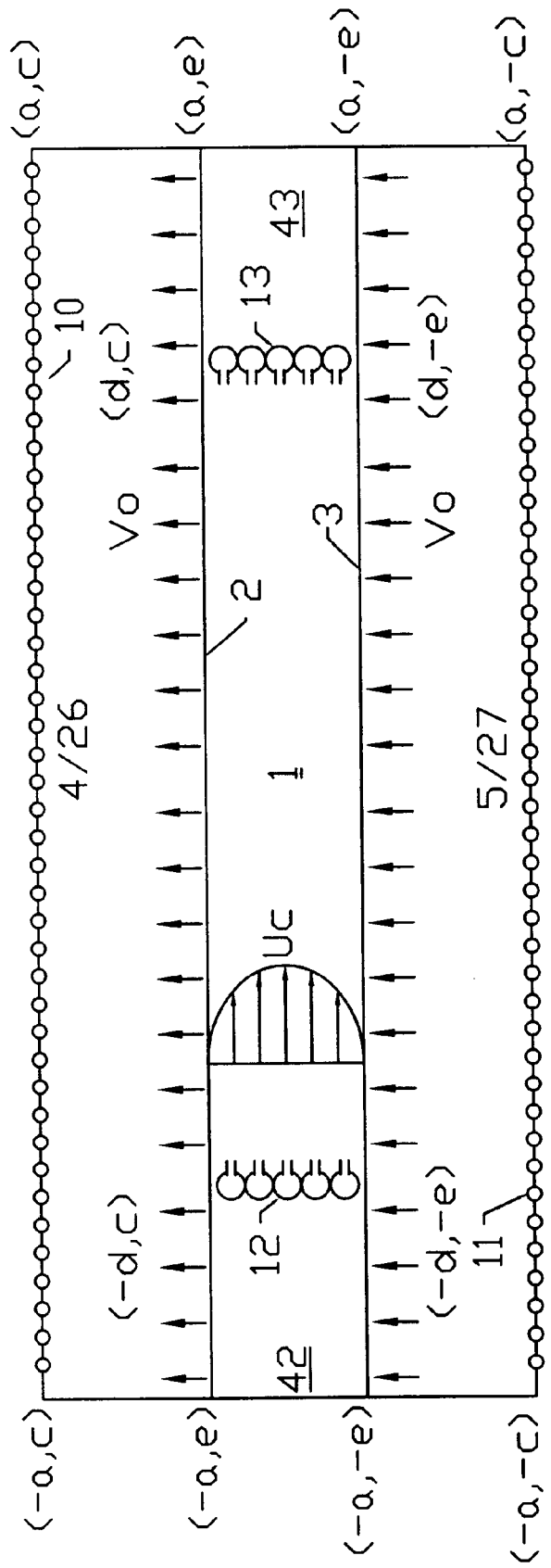
FIG. 7 is a side schematic view of a modified form of the separation chamber of the present invention.

FIGS. 4 and 5 show a multi-chamber configuration similar to the first two configurations. The separation chamber 1 is much wider in this case in order to accommodate the multitude of injection 12 and collection ports 13 necessary to handle the sample mobility spectrum of interest. The single electrodes of FIGS. 1 and 2 have been replaced with electrode arrays 10 and 11. Each element can be impressed with a specific voltage and is the mechanism by which the linear voltage gradient $E_Z$ is produced. For focusing, sample and buffer is injected through the port array 12 with the separated fraction streams collected at the exit port array 13. Flow occurs in the separation chamber 1 only between the port arrays 12, 13. Flow stagnation regions 42 and 43 respectively exist in front of port array 12 and in back of port array 13. The ports 21 and 24 are only active initially during filling of the chamber. These stagnation regions serve both as electrical current and the fluid flow return paths. FIG. 7 shows a simplified schematic of the chamber with a coordinate system to facilitate a description of the electrode and flow field needed for focusing and which will justify the port and electrode modifications described above.

The total rectangular chamber is bounded by:

$|x|<a$; $|y|<b$ and $|z|<c$, where y is the orthogonal axis to the x-z plane. The total chamber dimensions are double these values. It is separated into three segments by screens 2, 3 at $|z|=e$.

The linear electric field gradient $E_z$ is provided by electrode arrays 10 and 11 distributed along the line $|z|=c$ and are kept at the following voltages:

$$V = -\{Ax + Bz + \tfrac{1}{2}C(x^2 - z^2)\}$$

where the constants A, B and C are independent and computer controlled to optimize the separation. The purpose of these electrodes is to maintain this voltage V (which locally satisfies Laplace's equation, $\nabla^2 V = 0$) throughout the separation chamber 1 and its four adjacent segments 4, 5, 26, and 27. The insulating walls at $|y|=b$ do not modify this voltage distribution. The inflow and outflow ports 12, 13 at $|x|=d$ will not modify the electric field distribution provided each port is electrically isolated and there are adequate gaps in the z-direction between the ports, as FIG. 6 shows. The corresponding electric field components are:

$$E_x = A + Cx \quad (4)$$

$$E_z = B - Cz \quad (5)$$

Equation 5 produces focusing while equation 4 causes a linear variation in the axial ion motion affecting residence time which can be used to promote sample concentration.

Figure 8:
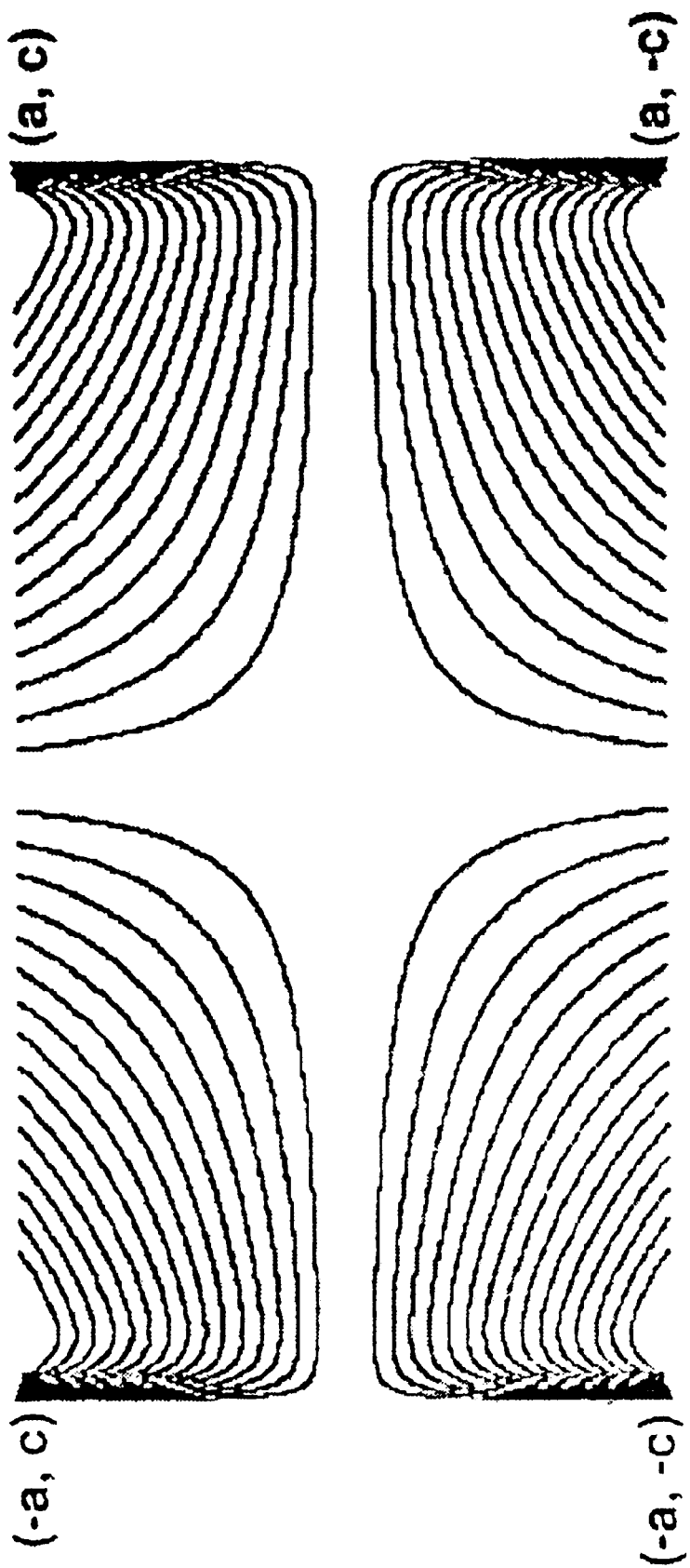
FIG. 8 is a graphic representation of the electric field lines of a numerical solution of equations relating to the electric field components of the apparatus of the present invention.

To see how equations 4 and 5 satisfy $\nabla^2 V = 0$, a numerical solution is done for the region bounded by $|z|=c$ and $|x|=a$. The boundary condition at $|z|=c$ is $$V = -\tfrac{1}{2}C(x^2 - z^2)$$

where $A=0$ and $B=0$ so that only the C terms are considered. The field lines for this solution are shown in FIG. 8. This computation was done for $a/c=20$; note that the z-dimension is exaggerated in the display. Note that the field lines indicate that equations 4 and 5 are good approximations except near the walls at $|x|=a$ and $|z|=c$. This region of conformity is bounded by $|z|=e$ and $|x|=d$ and is the separation chamber. The stagnation regions 42, 43 also provide a return path for the current converging near the walls at $|x|=a$. These return paths assure that $$E_z = B - Cz$$

in the separation chamber 1. In order to improve resolution, sample from the collection ports 13 can be recycled back into their corresponding entry ports 12 to form a recycling mode of operation. This mode will be a batch type for purposes of sample collection.

The preferred embodiment for detection and collection of the focused sample streams is to use a UV scan in front of the collection ports 13 to establish the position of the fractions and generate a conventional histogram for the fractions observed in the mobility spectrum currently under observation. One port should be used to collect a fraction of interest by positioning that fraction over the collection port by manipulation of either $V_o$ or $E_o$. This process is most easily handled through the use of computer control. Other fraction spectra can be observed and/or collected by further manipulation of $V_o$ or $E_o$.

As one of ordinary skill in this art would recognize, the above descriptive embodiments are only exemplary of the present invention, and there are numerous modifications and alternative modes that would fall within the scope of the invention, which is set forth in the claims appended hereto.

What is claimed is:

1. A method for separation and collection of at least one component from a mixture of components comprising the steps of:
   a. providing an apparatus comprising a separation chamber and a plurality of purge chambers, and establishing a first buffer flow in the separation chamber in the axial direction, said first buffer flow having a first flow rate;
   b. establishing a second buffer flow in each of at least two of said purge chambers in the axial direction, said second buffer flow having a second flow rate, said second buffer fluid flow having a second flow rate higher than that of the first flow rate;
   c. establishing a third buffer flow in a plurality of purge chambers axially adjacent to said separation chamber and separated from the separation chamber by metal-coated glass screens;
   d. establishing a fourth buffer flow into one of the purge chambers laterally through the separation chamber, then into and out of a second purge chamber to provide a uniform focusing fluid velocity in the separation chamber;
   e. introducing the mixture of components directly into the separation chamber flow entrance or through at least one injection port located in the separation chamber interior;
   f. applying an electrical potential transversely across the separation chamber in the form of a constant voltage gradient or a linearly varying voltage gradient to impart electrophoretic velocity to the fractional components in the separation chamber in the transverse direction perpendicular to the first buffer flow direction and parallel to the third buffer flow direction; and
   g. withdrawing at least one separated sample component.

2. A method according to claim 1 wherein the separated sample is withdrawn at the flow exit of the separation chamber.

3. A method according to claim 1 wherein the separated sample is withdrawn through a single collection port or from each of a plurality of collection ports.

4. A method according to claim 3 wherein the sample entering collection ports may be recycled back to the corresponding sample entry ports to form a recycling process which can improve resolution by increasing sample residence time.

5. A method according to claim 1 wherein the sample is injected with the carrier flow at the flow entrance of the separation chamber and is acted on by the combined influences of a constant electric field and said third flow transversely across the separation chamber.

6. A method according to claim 1 wherein one sample component is maintained in the separation chamber while extraneous components are discarded through the purge chambers.

7. A method according to claim 1 wherein the third buffer flow is adjusted to provide a transversely varying cross-flow velocity which allows any selected sample component to be either analyzed or collected.

8. A method according to claim 7 wherein the selected sample component is collected at the flow exit of the separation chamber.

9. A method according to claim 1 wherein the sample is injected through a single injection port into the separation chamber while carrier buffer enters the separation chamber at the fluid flow entrance of the separation chamber.

10. A method according to claim 9 wherein the sample is acted on by the combined influences of a constant electric field and said third buffer flow transversely across the separation chamber.

11. A method according to claim 10 wherein one sample fraction is maintained in the separation chamber and arrives at a single collection port in the separation chamber while extraneous components are either discarded through the said purge chambers or flow around the collection port and out of the separation chamber at the carrier buffer flow exit.

12. A method according to claim 1 wherein the said third buffer flow is adjusted to provide a transversely varying cross-flow velocity which allows any selected sample component to be either analyzed or collected at a single collection port.

13. A method according to claim 1 wherein the fraction spectrum of a sample may be analyzed or collected by varying the flow of a pump in a linear variation to present a time-dependent histogram.

14. A method according to claim 1 wherein the sample and buffer solution is injected through a plurality of input ports located at the entrance region of the separation chamber.

15. A method according to claim 14 wherein the sample fractions are acted on by the combined influences of a linearly varying electric field and a third buffer flow transversely across the separation chamber.

16. A method according to claim 1 wherein the sample fractions migrate toward set transverse positions near the exit end of the separation chamber.

17. A method according to claim 16 wherein the sample fractions may be scanned in the exit region of the separation chamber by a UV laser and detector system with sample fractions being collected in a single or multiple set of collection ports.

18. A method according to claim 17 wherein the sample fraction spectrum in the separation chamber is fixed by the transverse chamber thickness with the remainder of the spectrum being diverted through screens into and out of the purge chambers.

19. A method according to claim 18 wherein the sample fraction spectrum being viewed may be collected in singular or multiple collection ports by varying the third flow rate of focusing fluid velocity.

20. A method according to claim 16 wherein the sample fraction spectrum being viewed may be changed by varying the third flow rate of focusing fluid velocity.

* * * * *